United States Patent [19]

Howarth et al.

[11] Patent Number: 4,928,013

[45] Date of Patent: May 22, 1990

[54] TEMPERATURE INSENSITIVE MOISTURE SENSOR

[75] Inventors: John Howarth, Monte Sereno; Leonard M. Anderson, San Jose, both of Calif.

[73] Assignee: Measurex Corporation, Cupertino, Calif.

[21] Appl. No.: 14,870

[22] Filed: Feb. 17, 1987

[51] Int. Cl.$^5$ .............................................. G01N 21/35
[52] U.S. Cl. .................................. 250/339; 250/341; 250/358.1; 250/360.1
[58] Field of Search .................. 250/339, 358.1, 359.1, 250/360.1, 341, 343; 73/73

[56] References Cited

U.S. PATENT DOCUMENTS

| | | | |
|---|---|---|---|
| 3,405,268 | 10/1968 | Brunton | 250/339 |
| 3,641,349 | 2/1972 | Dahlin | 250/339 |
| 3,662,170 | 5/1972 | Keyes, IV | 250/339 |
| 3,793,524 | 2/1974 | Howarth | 250/343 |
| 3,851,175 | 11/1974 | Dahlin et al. | 250/339 |
| 4,345,150 | 8/1982 | Tamura et al. | 250/339 |
| 4,577,104 | 3/1986 | Sturm | 250/339 |
| 4,674,325 | 6/1987 | Kiyobe et al. | 73/159 |
| 4,766,315 | 8/1988 | Hellstrom et al. | 250/341 |

FOREIGN PATENT DOCUMENTS

| | | | |
|---|---|---|---|
| 1196512 | 11/1985 | Canada | 250/339 |
| 0164291 | 12/1985 | European Pat. Off. | 250/339 |
| 1182353 | 9/1985 | U.S.S.R. | 250/339 |
| 2044443 | 10/1980 | United Kingdom | 250/339 |

OTHER PUBLICATIONS

Vakulyuk et al., "Infrared Water-Content Meter for Paper," Measurement Techniques, vol. 19, No. 7, pp. 1065-1066, Jul. 1976.

Pugh, "The Infrared Measurement of Surface Moisture in Paper", Tappi, vol. 63, No. 10, pp. 131-134, Oct. 1980.

Primary Examiner—Janice A. Howell
Assistant Examiner—William F. Rauchholz
Attorney, Agent, or Firm—Spensley Horn Jubas & Lubitz

[57] ABSTRACT

An infrared paper web moisture sensor is described which comprises a source of infrared radiation for directing an infrared beam through the web and an infrared detecting unit disposed on the opposite side of the web from the infrared source. In one embodiment, the infrared detecting unit measures the transmission of the infrared beam through the web at three separate wavelength regions of the infrared spectrum, one of which is sensitive to web temperature. In a second embodiment, the infrared detecting unit measures the transmission of the infrared beam through the web at two separate wavelength regions of the infrared spectrum, one of which is insensitive to web temperature. For each embodiment, signals are developed indicative of the transmission of infrared through the web in each of these regions, digitized, and fed to the process control computer for the paper mill. The computer combines the values of the digitized signals, via an empirically derived equation, to produce a value indicative of the percentage of moisture in the web. The process control computer utilizes this result of control devices which selectively add moisture to portions of the web or selectively dry portions of the web to thereby produce a web having a uniform moisture content.

4 Claims, 1 Drawing Sheet

TEMPERATURE INSENSITIVE MOISTURE SENSOR

BACKGROUND OF THE INVENTION

The present invention relates to moisture sensors, and more particularly to a device and method for determining the moisture content of a paper sheet by measuring the transmission of various wavelengths of infrared radiation through the sheet. The measurement of the moisture content of the sheet is compensated for changes in the infrared absorption characteristics of water caused by changes in sheet temperature.

In the commercial manufacture of paper, paper is produced in a continuously moving sheet called a "web". Since the web is produced from an aqueous suspension including wood pulp fibers, cotton fibers and various chemicals, the web initially contains a considerable amount of moisture. Most of this moisture is removed during the paper making process. However, for a variety of reasons, it is desirable to maintain at least some moisture in the web. For example, if the web is too dry, it will tend to curl at the edges.

Paper web is normally dried by passing it around heated steel drying drums. However, this technique tends to dry the web unevenly. Such uneven drying produces paper of uneven quality. Hence, various devices have been developed to controllably moisten or dry only portions of the web, after the web has passed around the drying drums, to thereby produce a web having a uniform moisture content. Obviously, the paper mill operator, or the paper mill's process control computer, must know the moisture profile of the web before these moistening and drying devices can be used effectively. Web moisture sensors have therefore been developed which scan back and forth across the width of the web to determine its moisture content at various locations.

Water absorbs infrared radiation. Certain types of web moisture sensors take advantage of this phenomenon by directing a beam of infrared radiation at a web and measuring the intensity of the infrared beam after it passes through the web. The more moisture in a web, the greater the absorption of the infrared radiation.

Some of these infrared moisture sensors utilize two infrared detectors with an infrared band pass filter positioned in front of each detector. The pass band of each filter is chosen so that each detector receives energy only in a narrow region of the infrared spectrum. One filter is chosen to pass infrared radiation in a region of strong absorption by the water in the web. Thus, the detector associated with this filter is sensitive primarily to the amount of water in the web. This first detector receives more infrared radiation when the web is dry and less infrared radiation when the web is moist.

The band pass filter associated with the second detector is selected to pass infrared radiation in a portion of the infrared spectrum where there is relatively little absorption by moisture. In this second portion of the infrared spectrum, most of the infrared absorption is due to the web fibers themselves, not to the moisture in the web. Therefore, as the web fiber weight per unit area (i.e. the "basis weight") increases, this second detector receives less infrared radiation. The output of this second detector can thus be used to compensate the moisture measurements of the first detector for changes in the basis weight of the sheet. When the outputs from these two detectors are properly combined, these types of moisture sensors provide a measurement of the amount of moisture contained in the web or the percentage of moisture in the web, so that the moisture measurement is unaffected by changes in the basis weight of the sheet.

The intensity of the transmitted infrared beam is, however, not only dependent upon the moisture content of the web and its basis weight. The absorption of infrared radiation by the moist web also varies with the wavelength of the infrared rays. The water and web fibers absorb certain wavelengths of the infrared spectrum more effectively than other wavelengths so that there exists absorption peaks and valleys at various wavelengths along the infrared absorption spectrum. Moreover, these peaks and valleys shift to shorter wavelengths with increases in web temperature and to longer wavelengths with decreases in web temperature. However, the previously described infrared moisture measuring devices fail to compensate for shifts in the infrared absorption spectrum with changes in web temperature. Therefore, the moisture measurements of these devices are subject to significant error.

SUMMARY OF THE INVENTION

The present invention includes a method and a device which determine the moisture content of a paper web using measurements of the transmission of infrared radiation through the web at three separate wavelength regions of the infrared band. The device and method are primarily, but not exclusively, intended for on-line moisture measurements of a moving paper web on a paper making machine. In this situation, the moisture sensor of the present invention may be scanned back and forth across the width of the moving web (i.e. in the cross direction of the web) to thereby provide a measurement of the moisture content of the web at various positions along the length and width of the web. Signal processing circuitry and computer software associated with the sensor automatically compensate the moisture measurement for the effects, on infrared transmission through the web, of both changes in basis weight and changes in web temperature.

The infrared moisture sensor of the present invention includes a source of infrared radiation. A beam of infrared radiation is transmitted from this infrared source through the moving web. As the beam passes through the web, the water in the web and the web fibers absorb a portion of the infrared energy. The infrared beam contains a broad range of wavelengths. However, infrared radiation in certain wavelengths is preferentially absorbed by the moisture-containing web.

The moisture sensor also includes an infrared receiver. This receiver is positioned on the opposite side of the web from the infrared source and measures the intensity of the transmitted infrared beam in three separate wavelength regions of the infrared spectrum. The receiver comprises a beam splitter and three infrared detectors. The beam splitter directs a portion of the infrared beam at each of the three detectors. A separate infrared band pass filter is positioned before each detector. In this way, each of the infrared detectors measures the intensity of only the portion of the transmitted beam which falls within the pass band of the associated filter.

One of the three infrared band pass filters passes only infrared radiation having wavelengths on a slope of the absorption spectrum adjacent to the water absorption peak, for example, in the vicinity of approximately 1.90 microns. Infrared radiation having this wavelength is readily absorbed by water, but provides a stronger signal, when measuring the moisture content of a heavy, moist sheet, than if the pass band of the filter were centered directly over the absorption peak at about 1.93 microns. The output of the infrared detector associated with this first filter is therefore primarily dependent upon the moisture content of the web and the web temperature.

The second band pass filter passes only wavelengths in the region of the spectrum absorbed primarily by the paper fibers. Therefore, the intensity of the infrared beam detected by the detector behind this second filter is primarilyly indicative of the basis weight of the web. For example, the pass band or this second band pass filter may be positioned on the infrared transmission window for the paper fiber, for example at 1.85 microns. Positioning the pass band of this filter on this transmission window minimizes changes in the detected infrared intensity with changes in temperature. As discussed below, the output of this detector is used to correct the moisture measurement of the first detector for changes in the basis weight of the sheet. Thus, the present invention can provide a signal indicative of the percentage of moisture in the web, irrespective of changes in basis weight.

The third beam is filtered by a band pass filter which may advantageously pass only wavelengths at any one of several locations along the infrared spectrum. However, the pass band of this third band pass filter should be located on the absorption spectrum where the absorption of the infrared radiation by the moisture-containing web varies rapidly with wavelength. In other words, the pass band of this third filter should be located on a slope of the absorption spectrum between an absorption peak and an absorption valley. As previously mentioned, the infrared absorption spectrum for water shifts to shorter wavelengths with increases in temperature. Similarly, the infrared absorption spectrum for the web fiber (i.e. the wood pulp forming the web) also shifts to shorter wavelengths with increases in temperature. Thus, the output of the detector associated with this third filter will be sensitive to changes in sheet temperature. However, since the pass band of this third filter is located on a different portion of the absorption spectrum than the first band pass filter, the output from this detector will have a different temperature coefficient than the output of the first detector. Therefore, the output of this third detector may be used to correct the web moisture measurement of the first detector for the effects of changing web temperature on the infrared absorption characteristics of water.

According to the present invention, the outputs from the three detectors are combined, in an empirically determined formula, to yield an output which is indicative of the moisture content of the web. As previously explained, the output of one of the three detectors in the receiver of the present invention will be primarily affected by the amount and temperature of the moisture in the web between the infrared beam source and the receiver Therefore, this detector alone cannot give an accurate indication of the percentage of moisture in the web since this detector will receive less infrared radiation either (1) when the percentage of moisture increases or (2) when the percent of moisture in the web remains constant but the web basis weight increases. The amount of infrared radiation reaching this first detector will also be affected by shifts in the absorption spectrum caused by changes in web temperature. By monitoring the output of only this one detector, the paper mill operator (or the mill's process control computer) will be unable to differentiate between increases in the moisture content of the sheet, increases in basis weight and changes in web temperature. However, the filters associated with the second and third detectors are chosen so that the output of the second detector in the receiver varies primarily with changes in basis weight, while the output of the third detector varies primarily with changes in web temperature. Depending upon the location along the absorption spectrum of the third filter, the output of the third detector may also be sensitive to the moisture content of the sheet. However, by combining the output from the first detector in a weighted average with the output of the second and third detectors, the resulting combination can be made to indicate the amount of moisture in the web so that this indication is independent of both changes in web temperature and changes in basis weight.

The coefficients used in the formula for combining the outputs from the three detectors will depend, for example, upon the exact location of the band pass filters along the absorption spectrum and the width of the pass bands of these filters. The exact values for these coefficients can be determined empirically by measuring the outputs from each of the three detectors at a plurality of temperatures and basis weights and then choosing coefficients for the formula combining these outputs which minimize the temperature sensitivity of the resulting weighted average of the outputs.

Rather than utilizing three separate infrared detectors and a beam splitter to create three separate beams, the receiver half of the moisture sensor could be constructed using a single infrared detector and a mechanism for sequentially positioning each of the three band pass filters discussed above in front of the single detector. With this configuration, the output from the detector is determined at different times corresponding to the times when each of the three filters is in the path of the infrared beam. The outputs of the detector, corresponding to the times when each of the three filters is positioned before the detector, is then combined in the same manner as explained above in connection with the three detector embodiment to yield a moisture measurement which is insensitive to changes in web temperature. According to another aspect of the present invention, a temperature insensitive paper web moisture sensor comprises an infrared radiation source for directing a beam of infrared radiation through a sheet of paper and detecting means for detecting the amount of infrared radiation from the beam which transmits through the sheet in first and second separate wavelength regions of the infrared spectrum. The first region is positioned around the infrared absorption peak for water so that the intensity of the infrared radiation transmitted through the sheet in the first region is substantially insensitive to the temperature of the sheet and the second region is selected to detect infrared radiation which is primarily sensitive to the amount of paper fiber in the path of the infrared beam.

DETAILED DESCRIPTION OF THE PREFERRED EMBODIMENTS

The following description is of the best presently contemplated modes of carrying out the invention. This description is made for the purpose of illustrating the general principles of the invention and should not be taken in a limiting sense. The scope of the invention is best determined by reference to the appended claims.

Figure 1:
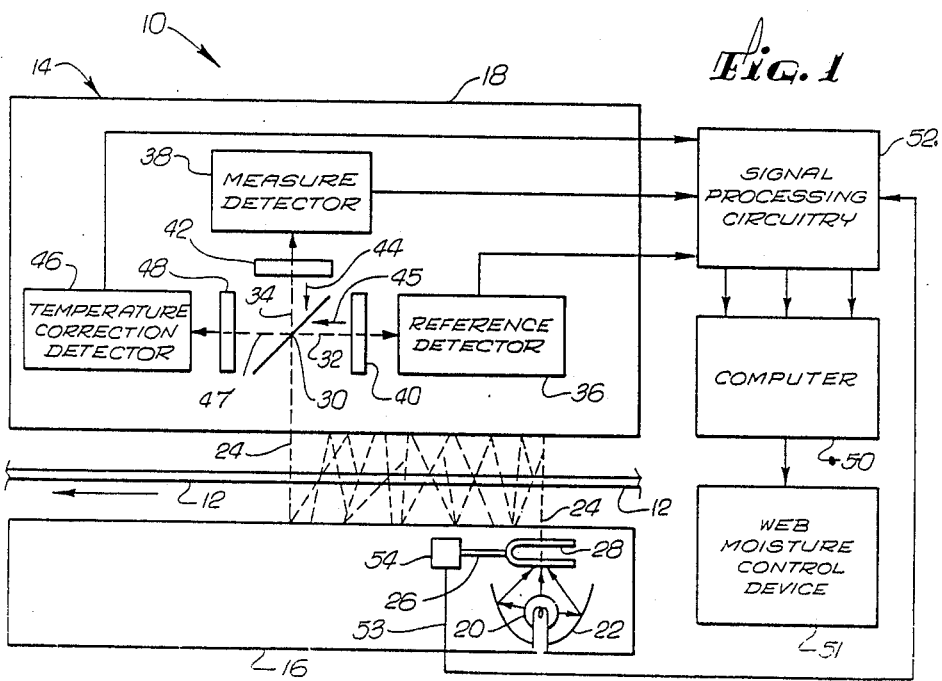
FIG. 1 illustrates a temperature compensating moisture sensor constructed according to the present invention.

The present invention includes the infrared moisture sensing device 10 illustrated in FIG. 1. This device is used to measure the moisture content of a paper web 12 and to automatically compensate this measurement both for changes in the basis weight of the web 12 and the web temperature. To accomplish this measurement, the device of FIG. 1 uses a sensor 14 which may be thought of as having two halves, a source half 16 and a receiver half 18, disposed on opposite sides of the paper web 12.

The infrared source 16 uses an incandescent lamp 20 and an eliptical reflector 22 to direct a beam of infrared radiation 24 through a moving paper web 12. It is preferred, but not necessary to the invention, that the amount of infrared radiation exiting the source 16 and impinging upon the web 12 be modulated at a known frequency. This modulation may be accomplished by any one of several devices. For example, as illustrated in FIG. 1, the tines 28 of a tuning fork 26 may be disposed in the path of the infrared beam 24. The vibrating tines 28 modulate the infrared light beam 24 as the tines 28 move alternatively into and out of the path of the beam 24. Alternatively, an opaque disk (not shown) having a plurality of evenly spaced radial slots, may be rotated in the path of the beam so that the beam is alternately transmitted through the slots and blocked by the opaque portions of the disk. With either device, the beam 24 is modulated at a known frequency. The reason for modulating the beam is explained below.

In the embodiment illustrated in FIG. 1, it is also preferred, but not necessary to the invention, that the beam be reflected back and forth between the source 16 and receiver 18 sides of the sensor 14 before entering the receiver 18. Reflecting the infrared beam 24 repeatedly between the source 16 and receiver 18 so that the beam passes a plurality of times through the web 12 provides certain advantages when measuring the moisture content of very light grades of paper, such as tissue, and very heavy paper grades. The advantages of such multiple reflections are more fully discussed in U.S. Pat. No. 3,793,524, incorporated herein by reference and assigned to the same assignee as the present application. Alternatively, the beam 24 may be directed in a single straight line from the source 16 to the receiver 18 so that the beam 24 only passes once through the web 12.

The receiver portion of the present invention 18 includes a beam splitter 30 which splits the beam 24 from the infrared source 16 into two separate beams, 32 and 34. Each of these beams is directed at separate band pass filters 40, 42 positioned in the path of each of the two beams 32, 34 immediately before the lead sulfide detectors 36, 38. Each filter 40, 42 is selected so that it passes infrared radiation in a separate portion of the infrared band. Infrared radiation not within the pass band of the filters 40, 42 is reflected by these filters back to the beam splitter 30 (as shown at reference numerals 44 and 45) and thus does not reach these reference or measure detectors 36, 38. However, the reflected beam 44 impinges upon the beam splitter 30 and the beam splitter 30 directs some of the beam 44 to a third filter 48. Moreover, some of the infrared beam 32 is reflected from filter 40 (as shown at 45), where it passes through the beam splitter to combine with the portion of the beam 44 reflected by the beam splitter toward filter 48. The combined beam is shown by reference numeral 47. Thus, with the moisture sensor of the present invention, a single beam 24 enters the receiver 18, but the optics within the receiver splits up the beam 24 into three separate beams, 32, 34, and 47, each detected by a different infrared detector, 36, 38 and 46.

The pass band of each of the three filters 40, 42 and 48 is selected so that the wavelengths of the radiation reaching each of the three detectors 36, 38 and 46, and thus the signal from each detector, is affected by the web basis weight, the amount of moisture in the web and the web temperature, respectively. Using these three signals, and the equations discussed below, a process control computer 50 periodically computes the moisture content of the web 12. Furthermore, by scanning the sensor 14 back and forth in the cross direction of a moving web 12 as the web 12 is produced in a paper mill, the device of the present invention can provide signals indicative of the moisture content of the web 12 at various locations across the length and width of the web 12. These moisture measurements can then be used to selectively control various well known devices 51 for increasing or decreasing the moisture content of portions of the web 12, thereby providing a web 12 having a uniform moisture content across its width and along its length.

Based upon the results of the moisture measurements, a web moisture correction can be accomplished manually. However, many modern paper mills are highly automated. In these mills, the signals produced by the sensor 10 of the present invention are preferably fed to a central process control computer 50 which computes the web moisture profile using these signals from the three infrared detectors 36, 38 and 46 and then, based on this computation, selectively activates any one of a number of known devices 51 for altering the moisture content of certain portions of the web 12. Many such devices for altering the web moisture profile exist, including such devices as selectively controllable water showers for increasing the moisture content of sections of the web 12 and infrared heaters for selectively drying sections of the web 12.

Figure 2:
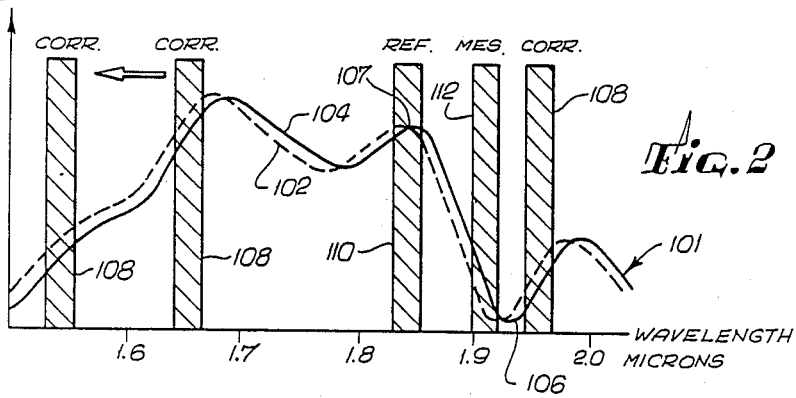
FIG. 2 illustrates an infrared transmission spectrum for a medium weight paper web containing moisture.
Figure 3:
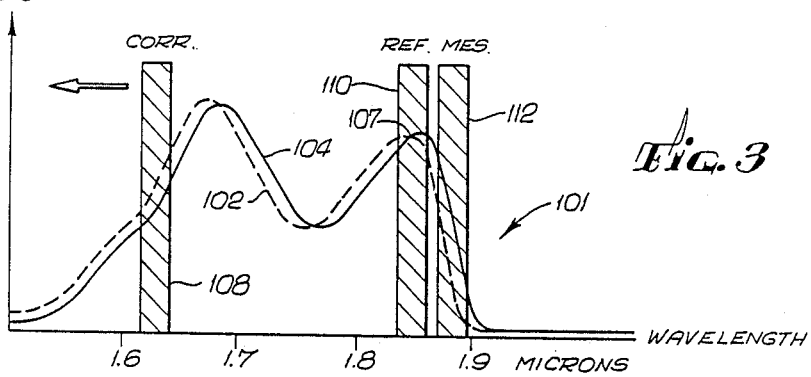
FIG. 3 illustrates an infrared transmission spectrum for a moist, heavy weight paper web.

FIGS. 2–3 illustrate infrared transmission spectra 101 for moisture-containing medium and heavy weight paper webs, respectively. As best illustrated in FIG. 2, the absorption of infrared radiation at some wavelengths is more effective than at other wavelengths. Absorption at the shorter wavelengths of the spectrum, i.e. below about 1.9 microns, is predominantly dependent upon absorption by the paper web fibers. Conversely, at the longer wavelength end of the spectrum, above approximately 1.9 microns, water is more efficient at absorbing infrared radiation than the web fibers. Hence, the longer wavelength portion of the spectrum is prominently affected by the moisture content of the web. For example, the absorption peak for water (corresponding to minimum infrared transmission) occurs at a wavelength of approximately 1.93 microns. Nevertheless, the entire infrared spectrum is absorbed, at least to some extent, by water in the web.

The infrared absorption spectrum of water and paper is peculiar in that the absorption characteristics of the entire spectrum shift to shorter wavelengths as the web temperature is increased and to longer wavelengths as the web temperature decreases. The infrared spectrum of a moist sheet at higher temperatures is shown by the dashed line 102 of FIGS. 2 and 3. The solid line 104 in these two figures shows the same absorption features, but at longer wavelengths because the web temperature is lower than for the spectra illustrated by the dashed line 102.

With the technique of the present invention, an infrared band pass filter 42 (FIG. 1) associated with the measure detector 38 has its pass band 112 on a slope of the transmission spectrum adjacent to the absorption peak 106. Because the pass band 112 of this filter is near the absorption peak 106, the signal from the measure detector 38 is strongly dependent upon the moisture content of the web 12. The signal from this detector (hereinafter the "MES" signal) provides a rough measurement of the web moisture content.

The advantage of positioning the pass band of the filter 42 associated with the measure detector 38 on a slope is that less infrared radiation is absorbed at this wavelength than at the absorption peak 106 and thus the measure detector 38 receives a stronger infrared signal. However, at the same time, since the pass band 112 is positioned on a sloping region of the transmission spectrum, the measure detector signal becomes more sensitive to changes in web temperature than if the pass band 112 of the filter 42 were centered around the absorption peak 106. It is preferred that the pass band 112 be located between about 1.85–1.93 microns.

Because the output of the measure detector 38 will be sensitive to variations in web temperature, the present invention provides a second infrared detector 46 with an associated infrared band pass filter 48. The signal from this detector 46 (hereinafter the temperature correction detector) is used to correct the moisture measurement of the measure detector 38 for the effects of varying web temperature. The pass band chosen for this second band pass filter 48 may be any one of a number of alternatives. The pass band 108 for the band pass filter 48 of this temperature correction detector 46 is placed on a slope of the transmission spectrum 101 so that the amplitude of the signal from the temperature correction detector 46 is highly dependent upon changes in web temperature. The changes in the signal from the temperature correction detector (hereinafter the "CORR" signal) are used to compensate for the temperature induced changes in the MES signal. Some possible positions for the pass band 108 of this filter are shown in FIG. 2. For example, the CORR pass band locations between 1.55–1.67 microns are shown toward the left side of FIG. 2 and the CORR pass band locations between 1.94–1.98 microns are shown on the right side of FIG. 2. The hatched areas in this figure illustrate possible locations for the pass bands within these wavelength ranges.

As the paper web 12 gets heavier, however, the choice of band pass wavelengths for the CORR signal become more restricted, until the condition shown in FIG. 3 exists. FIG. 3 illustrates an infrared transmission spectrum 101 for a moist, heavy sheet. For this sheet, the sloping portion of the transmission spectrum around 1.6 microns becomes the preferred region for the pass band 108 of the filter 48.

As previously mentioned, the infrared absorption spectrum is also affected by the basis weight of the web 12. To provide a signal predominantly dependent upon the basis weight of the web 12, a band pass filter 40 is positioned before the reference signal detector 36. This filter 40 has a pass band 110 (FIGS. 2–3) in a region of the infrared transmission spectrum 101 which is absorbed predominantly by the web fibers. For example, in the presently preferred embodiment, the band pass filter 40 has a pass band in the wavelength range of from about 1.7 to about 1.9 microns. The detector 36 associated with this filter 40, called the reference signal detector, provides an output the amplitude of which is predominantly affected by the mass of the paper fibers per unit area of the web 12 through which the infrared beam 24 passes. As the web basis weight increases, the amount of infrared radiation which passes through the web 12 decreases. The signal from this reference detector 36 (hereinafter the "REF" signal), as described below, is used to compensate the measured moisture value for changes in the basis weight of the web 12. It is especially preferred that the pass band 110 of filter 40 be located at a portion of the infrared absorption spectrum affected primarily by web fiber (i.e. below 1.9 microns) but which is also relatively insensitive to changes in web temperature, for example, near the transmission peak 107 shown in FIGS. 2–3, around 1.83–1.85 microns.

As previously mentioned, the infrared energy from the infrared source 16 is sinusoidally modulated by the tines 28 of the vibrating tuning fork 26. Thus, the output of each infrared detector 36, 38 and 46, is also sinusoidally modulated at the same frequency and phase as the detected infrared beams 32, 34 and 44. However, infrared energy from the paper web 12 itself and from other external sources (not shown) will also reach the detectors 36, 38 and 42. Thus, each detector signal also includes a DC component.

The output of each of the three detectors 36, 38 and 46 is transmitted to the signal processing circuitry 52. This circuitry is designed to filter out the DC component of the detector signals. The filtered detector signals are then passed on to a phase synchronous demodulation circuit included within the signal processing circuitry 52. The purpose of the phase synchronous demodulator is to filter out changes in the signals from the detectors 36, 38 and 46, which changes are not caused by the varying infrared absorption of the web 12. For example, 60Hz line noise in the detector signals is filtered out by the demodulator circuit, as explained below.

A sine wave oscillator 54 is used to drive the tines 28 of the tuning fork 26 at the resonant frequency of the tuning fork 26. The output of this sine wave oscillator 54 is first converted to a square wave having the same frequency and phase as the sine waves driving the tuning fork 26. This square wave output 53 is fed to the phase synchronous demodulator portion of the signal processing circuitry 52, along with the filtered signals from each of the three infrared detectors 36, 38 and 46. The signals from the infrared detectors 36, 38 and 46 are, of course, modulated at the same frequency and phase as the output of the oscillator 54. Hence, by demodulating the outputs from each detector 36, 38 and 46 with a square wave having the same frequency and phase as the output of the tuning fork oscillator 54, and then averaging the demodulated outputs over a number of cycles, the moisture sensing device 10 of the present invention filters out changes in the detector signals which result from changes in the intensity of external infrared sources, or extraneous signals such as the 60Hz line voltage. This filtering technique using a phase synchronized demodulation circuit is well known. Changes in the intensity of the infrared energy reaching the detectors 36, 38 and 46 from other external sources or from the power line would, of course, provide an erroneous moisture content measurement.

The averaged amplitude of each of the demodulated signals from each detector is indicative of the amount of infrared transmission through the web within the pass band of the filter associated with each detector. The amplitude of these amplitude averaged and demodulated detector signals is then measured by the signal processing circuitry, digitized, and fed to the process control computer 50. This computer 50 computes the moisture content of the web 12 utilizing the equations and techniques described below The resulting computed value of the web moisture content is indicative of the amount of moisture in the web 12, irrespective of the web temperature and basis weight.

The computer combines the digitized detector amplitude signals to achieve an output indicative of the moisture content of the web 12 according to any one of a number of possible equations. These equations combine values indicative of the amplitudes of each of the detector signals to achieve a weighted average of these three values. The weighting coefficients of the equations are dependent upon the width of the pass bands of each filter and their locations on the absorption spectrum 101. The coefficient values are chosen empirically to provide the weighted average of the detector signal values with minimal sensitivity to changes in temperature and basis weight. One presently preferred moisture calculation proceeds as follows:

A water ratio R1, which is a rough measure of the water weight per unit area of the web, is given by the formula $R1 = REF/MES$. A second ratio R2, which is influenced by the web temperature, is calculated as: $R2 = REF/CORR$. The REF or reference value, as previously mentioned, is primarily sensitive to the basis weight of the web, whereas the MES or measurement value is primarily sensitive to the moisture content of the web. The CORR, or correction value, is dependent upon the web temperature.

The ratios R1 and R2 are then combined to give a third ratio, RT, which is indicative of the amount of water in the web but which is highly insensitive to web temperature. As previously mentioned, the exact formula for combining the ratios Rl and R2 depends on the wavelengths chosen to produce the detector signals. If the chosen CORR wavelength is strongly sensitive to the amount of moisture in the sheet, for example, if the CORR wavelength is chosen, as shown in FIG. 2, around 1.97 microns, then $RT = R1 + C1*(R2 - C2)$. This formula describes RT, the water content indicator, as being equal to R1, the temperature sensitive water ratio plus a term, $C1*(R2-C2)$, which is a function of the temperature compensating ratio, R2. In other words, RT is set equal to a weighted average of the two temperature sensitive ratios, Rl and R2, which change in different ways with temperature. In the case illustrated in FIG. 2, wherein the REF filter is positioned near 1.85 microns, the MES filter is positioned near 1.9 microns and the CORR filter is positioned near 1.97 microns, the ratios R1 and R2 change with opposite signs. That is, as one ratio gets larger the other ratio decreases.

In the above equation for RT, C1 and C2 are constants which are chosen to minimize the temperature dependence of RT. R1 will be equal to approximately 1 when the web is completely dry. Similarly, R2 will be approximately equal to 1 when the web is completely dry. The value of R2 for the dry web may deviate slightly from 1, however, since the REF and CORR wavelengths may be sufficiently separated along the wavelength spectrum that the difference in absorption of the dry paper at these two wavelengths will not be equal. Thus, by setting C2 at the value of R2 for a perfectly dry sheet, RT will equal R1 when the sheet is dry.

The optimal values for C1 and C2 may be determined by taking readings of the MES, REF and CORR signals using samples of moisture-containing paper which are sealed between two plates of glass. The glass serves, not only to maintain constant moisture values within the paper sheets during the calibration measurements, but also to provide a thermal mass which maintains the temperature of the sheets sufficiently long to make possible a series of measurements at decreasing temperatures above ambient temperature. To accomplish this, the glass-enclosed sheets are first heated. Then, measurements of the infrared penetration through the glass enclosed sheets are made periodically as the temperature of the glass enclosed sheets decreases. By obtaining values of the ratios of R1 and R2 over a range of temperatures, the values of C1 and C2 can be chosen to minimize the sensitivity of RT to changes in temperature.

Another presently preferred equation for the water content indicator, for use when the CORR value is sensitive to web moisture content, is: $RT = \frac{1}{2}[C1(R1-D1) + C2(R2-D2)]$. In this equation, D1 and D2 are constants having values equal to the values of R1 and R2, respectively, for the dry sheet at or near its average temperature at the sensor location. In the commercial manufacture of paper, many web processing steps occur at elevated temperatures. Thus, the average sheet temperature at the sensor location is frequently above the ambient temperature. As with the previously discussed formula, C1 and C2 are chosen to minimize the sensitivity of RT to changes in web temperature.

If the CORR wavelength is not strongly sensitive to the water content of the sheet, then a different equation than those described above is preferred. For example, if the CORR pass band is positioned around 1.6 microns, then $RT = R1*(1 + C1*(R2 - C2))$. As in the first described formula, this third formula computes RT, the water content indicator, as being equal to R1, the temperature sensitive water ratio, plus a term, $C1*(R2 - C2)$, which is a function of the temperature compensating ratio, R2. However, because the CORR signal in this instance is insensitive to the web moisture content, this second formula multiplies the term $C1*(R2-C2)$ by R1 to thereby weight the $C1*(R2-C2)$ correction factor according to the amount of water in the web. Moreover, as in the previously described formulas, C1 and C2 are chosen empirically to minimize the sensitivity of RT to web temperature.

The process control computer 50, can calculate the water weight per unit area from any of the above formulas using the linear equation $WW = A*RT + D$, wherein A and D are the slope and intercept, respectively, of the line defined by the linear equation, and WW is the water weight per unit area of the sheet. From this latter equation, the percentage of moisture in the sheet can then be calculated using an auxiliary measurement of the weight per unit area of the web, BW.

Thus, the percent moisture content of the web is calculated by the process control computer 50 by multiplying 100* WW/BW.

Another embodiment of the present invention eliminates the need for the third temperature correction detector 46. In this embodiment, a first band pass filter, associated with the measure detector, is selected so that it passes infrared in the portion of the infrared spectrum approximately centered around the infrared absorption peak for water, i.e. about 1.93 microns. In this way, as the web temperature increases, for example, the intensity of detected infrared radiation increases at the long wavelength side of the pass band of the filter, while an approximately equal decrease in detected infrared radiation occurs at the opposite short wavelength side of the pass band. With this technique, the total amount of infrared radiation reaching the measure detector, and hence the MES signal, is relatively insensitive to web temperature. Thus, a temperature compensating CORR signal is not necessary. A reference detector is, however, also used in the manner previously described to provide a signal to the process control computer indicative of the amount of paper fiber per unit area of the web. With this two detector embodiment of the present moisture sensor, RT may simply be set equal to R1.

Three embodiments of the device of the present invention have been described. With these embodiments, the process control computer of a modern automated paper mill can continuously measure the moisture content of a moving paper web at a number of locations across the length and width of the web. The moisture measurements are compensated for changes in the temperature and the basis weight of the web. With these temperature and basis weight compensated moisture measurements, the paper mill process control computer can selectively activate various previously known devices for increasing and decreasing the moisture content of portions of the web to thereby produce high quality paper having a uniform moisture content. As previously mentioned, water showers and infrared lamps, for example, may be used to control the web moisture content.

From the above, one skilled in the art will understand that many modifications may be made to the optical system and the processes described herein without departing from the spirit and scope of the invention. For example, the pass bands of the filters in the receiver half of the sensor may be chosen at values other than those shown in FIGS. 2-3. Also, the equations may be changed or modified For example, in the equation RT=R1+C1* (R2−C2), the C1*C2 term resulting from the multiplication of these two constants may be deleted In that case, a completely dry sheet would not provide an RT value of 1, but the RT value would still be equally insensitive to changes in web temperature. Moreover, measurements of the infrared transmission at four or more separate wavelength regions of the infrared transmission spectrum may be made and these measurements combined in a weighted average to yield a value indictive of the web moisture content, which combination is insensitive to changes in web temperature and basis weight. Thus, the invention is not limited to the specific embodiments described herein.

We claim:

1. A paper web moisture sensor insensitive to web temperature, comprising:
   an infrared radiation source for directing a beam of infrared radiation through a sheet of paper; and
   detecting means for detecting the amount of infrared radiation from the beam which transmits through the sheet in first and second separate wavelength regions of the infrared spectrum, wherein said first region is positioned around the infrared absorption peak for water so that the intensity of the infrared radiation transmitted through the sheet in the first region is substantially insensitive to the temperature of the sheet and the second region is selected to detect infrared radiation which is primarily sensitive to the amount of paper fiber in the path of the infrared beam.

2. The paper sheet moisture sensor of claim 1, wherein the first region is positioned around 1.93 microns and the second region is positioned within the wavelength region from 1.83-1.85 microns.

3. A process for adjusting the moisture content of a paper web, comprising the steps of:
   (a) directing a beam of infrared radiation through the web;
   (b) moving the beam relative to the web;
   (c) measuring, at a plurality of locations along the web, the amount of infrared energy transmitted through the web in first and second separate regions of the infrared spectrum, wherein the first region is positioned around the infrared absorption peak for water and the long and short wavelength boundaries of the first region are so chosen that the amount of infrared energy transmitted through the web in the first region is substantially independent of the web temperature, and the second region is located at a part of the infrared transmission spectrum absorbed primarily by paper fibers;
   (d) calculating, with a computer, the moisture content of different portions of the web using the measurements of the infrared transmission for the first and second regions of the infrared band; and
   (e) altering the moisture content of at least a portion of the web based upon the calculated moisture content of the different portions of the web.

4. A paper web moisture sensor, comprising:
   an infrared radiation source for directing a beam of infrared radiation through a sheet of paper;
   detecting means for detecting the amount of infrared radiation from the beam which transmits through the sheet in a first and second separate wavelength regions of the infrared spectrum, wherein the first region is positioned around the infrared absorption peak for water and the long and short wavelength boundaries of the first region are so chosen that the amount of infrared energy transmitted through the web in the first region is substantially independent of the web temperature, and the second region is located at a part of the infrared transmission spectrum absorbed primarily by paper fibers; and
   means for calculating the moisture content of the web using the detected amount of infrared radiation for the first and second regions of the infrared spectrum.

* * * * *

UNITED STATES PATENT AND TRADEMARK OFFICE
CERTIFICATE OF CORRECTION

PATENT NO. : 4,928,013
DATED : May 22, 1990
INVENTOR(S) : John Howarth, et al.

It is certified that error appears in the above-identified patent and that said Letters Patent is hereby corrected as shown below:

In the Abstract, line 20, after "web" insert --, which value is not affected by changes in web temperature--.

Column 3, line 15, delete "or" and substitute --of--.

Column 3, lines 60-61, after "receiver" insert --.--.

Column 7, line 41, after "alternatives" insert --.--.

Column 11, line 50, after "modified" insert --.--.

Column 11, line 53, after "deleted" insert --.--.

In claim 2, line 20, after "from" insert --about--.

Signed and Sealed this

Tenth Day of March, 1992

Attest:

HARRY F. MANBECK, JR.

*Attesting Officer*　　　　*Commissioner of Patents and Trademarks*